US012005246B2

(12) United States Patent
Pahlevan et al.

(10) Patent No.: US 12,005,246 B2
(45) Date of Patent: Jun. 11, 2024

(54) VESSEL COMPRESSION WITH HEMODYNAMIC WAVE REFLECTION TO CONTROL VASCULAR WAVE DYNAMICS AND ENHANCE BLOOD FLOW

(71) Applicant: California Institute of Technology, Pasadena, CA (US)

(72) Inventors: Niema M. Pahlevan, Pasadena, CA (US); Morteza Gharib, Altadena, CA (US); Marie Csete, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 17/143,068

(22) Filed: Jan. 6, 2021

(65) Prior Publication Data

US 2021/0205598 A1    Jul. 8, 2021

Related U.S. Application Data

(60) Provisional application No. 62/957,621, filed on Jan. 6, 2020.

(51) Int. Cl.
| | |
|---|---|
| *A61M 60/161* | (2021.01) |
| *A61L 27/36* | (2006.01) |
| *A61L 27/52* | (2006.01) |
| *A61M 60/289* | (2021.01) |
| *A61M 60/465* | (2021.01) |

(52) U.S. Cl.
CPC ....... *A61M 60/161* (2021.01); *A61L 27/3625* (2013.01); *A61L 27/52* (2013.01); *A61M 60/289* (2021.01); *A61M 60/465* (2021.01)

(58) Field of Classification Search
CPC ..... A61M 60/00; A61M 60/40; A61M 60/289
See application file for complete search history.

(56) References Cited

U.S. PATENT DOCUMENTS

| | | | | |
|---|---|---|---|---|
| 4,583,523 A | * | 4/1986 | Kleinke | A61M 60/892 600/16 |
| 4,809,676 A | * | 3/1989 | Freeman | A61M 60/148 601/134 |
| 5,273,518 A | * | 12/1993 | Lee | A61M 60/468 623/3.12 |
| 2005/0020874 A1 | * | 1/2005 | Lau | A61N 1/3627 600/37 |
| 2007/0038016 A1 | * | 2/2007 | Gharib | A61M 60/122 417/474 |
| 2008/0194905 A1 | * | 8/2008 | Walsh | A61F 2/07 600/17 |

(Continued)

*Primary Examiner* — Rex R Holmes
*Assistant Examiner* — Jennifer L Ghand
(74) *Attorney, Agent, or Firm* — Knobbe Martens Olson & Bear, LLP

(57) ABSTRACT

A system configured to be at least partially implanted along an aorta includes an inelastic, static member and a pinching member. The pinching member is configured to receive an activation signal at an activation rate and in response to the activation signal, repeatedly compress the aorta at the second location at the activation rate to pump fluid within the aorta in a desired pumping direction. The system is configured to selectively control wave reflections in order to achieve both improved wave dynamics to reduce cardiac load and increased (or at least non-diminished) blood flow to targeted organs within the cardiovascular system.

19 Claims, 4 Drawing Sheets

(56) References Cited

U.S. PATENT DOCUMENTS

| | | | |
|---|---|---|---|
| 2012/0053672 A1* | 3/2012 | Gharib | A61M 60/135 |
| | | | 607/9 |
| 2016/0045654 A1* | 2/2016 | Connor | A61M 60/237 |
| | | | 600/16 |
| 2016/0144091 A1* | 5/2016 | Breedon | A61F 2/0036 |
| | | | 264/129 |
| 2016/0317729 A1* | 11/2016 | Criscione | A61N 1/39622 |

* cited by examiner

VESSEL COMPRESSION WITH HEMODYNAMIC WAVE REFLECTION TO CONTROL VASCULAR WAVE DYNAMICS AND ENHANCE BLOOD FLOW

CROSS-REFERENCE TO RELATED APPLICATIONS

The present application claims priority from U.S. Provisional No. 62/957,621, filed Jan. 6, 2020, which is incorporated by reference herein in its entirety.

TECHNICAL FIELD

The invention relates generally to methods and devices that can treat symptoms and conditions in the vascular system as well as the field of wave optimization technology.

BACKGROUND

A healthy cardiovascular system operates based on a delicate balance between its mechanical characteristics (contractility, compliance, preload, afterload) and the wave dynamics and hemodynamics of the vascular network. The pumping mechanism of the heart is pulsatile. Waves are generated in the aorta when the pulsatile flow enters the compliant aorta. These waves propagate and are reflected at numerous reflection sites in the vascular system. These reflection sites have different forms such as branching points, altered wall properties, and changes in wall diameters (e.g., tapering). Wave reflections can significantly influence the hemodynamics of large vessels such as the ascending, descending and abdominal aorta.

Recent studies by Pahlevan and Gharib (N. M. Pahlevan, M. Gharib, In-vitro investigation of a potential wave pumping effect in human aorta, *Journal of biomechanics* 46, 2122-2129 (2013), incorporated by reference herein) showed that aortic waves in the human aorta create a pumping effect similar to that of an impedance pump. An impedance pump is a simple pumping mechanism driven by waves. In its simplest from, impedance pumps can be considered a single elastic tube with reflection sites at both ends and at sites that can be created by pinching the elastic tube. As a pincher deforms the wall of the elastic tube, waves are generated inside the tube and propagate toward the reflection sites, where they are reflected. Depending on the dynamics of the waves, pumping occurs inside the elastic tube in a particular direction and with variable magnitude.

These phenomena have been extensively studied in Dr. Gharib's research group at Caltech (see, I. Avrahami, M. Gharib, Computational studies of resonance wave pumping in compliant tubes, *Journal of Fluid Mechanics* 608, 139-160 (2008); A. S. Forouhar, M. Liebling, A. Hickerson, A. Nasiraei-Moghaddam, H.-J. Tsai, J. R. Hove, S. E. Fraser, M. E. Dickinson, M. Gharib, The Embryonic Vertebrate Heart Tube Is a Dynamic Suction Pump, *Science* 312, 751-753 (2006) (published online Epub May 5, 2006 (10.1126/science.1123775)); A. Hickerson, D. Rinderknecht, M. Gharib, Experimental study of the behavior of a valveless impedance pump, *Experiments in Fluids* 38, 534-540 (2005)10.1007/s00348-005-0946-z; A. I. Hickerson, M. Gharib, On the resonance of a pliant tube as a mechanism for valveless pumping, *Journal of Fluid Mechanics* 555, 141-148 (2006); L. Loumes, I. Avrahami, M. Gharib, Resonant pumping in a multilayer impedance pump, *Physics of Fluids* 20, 023103 (2008); D. Rinderknecht, A. I. Hickerson, M. Gharib, A valveless micro impedance pump driven by electromagnetic actuation, *Journal of Micromechanics and Microengineering* 15, 861-866 (2005), all of which are incorporated by reference herein).

In a recent study by Pahlevan and Gharib (N. M. Pahlevan, M. Gharib, A Bio-Inspired Approach for the Reduction of Left Ventricular Workload, *PLoS ONE* 9, e87122 (2014) 10.1371/journal.pone.0087122), it was shown that wave reflection can be optimized inside the aorta by simply inserting a ring around the aorta. The ring acts as a wave reflection site, and depending on the state of the cardiovascular system, can be used to optimize wave reflection. The wave optimization can be achieved by inserting the ring at a proper location along the aorta and at a specific range of heart rates. The optimized wave reflection phenomenon reduces the workload on the heart and increases coronary artery blood flow. The Pahlevan and Gharib study indicates that small changes in wave dynamics can create considerable effect on the efficiency of the systemic circulation. Id.

A separate study showed that neonatal cardiomyocytes grafted in the wall of the abdominal aorta or inferior vena cava of rats survive, grow, and then spontaneously contract within the wall (W. Dai, S. L. Hale, R. A. Kloner, Implantation of Immature Neonatal Cardiac Cells Into the Wall of the Aorta in Rats: A Novel Model for Studying Morphological and Functional Development of Heart Cells in an Extracardiac Environment, *Circulation* 110, 324-329 (2004) (published online; W. Dai, S. L. Hale, R. A. Kloner, Development of a spontaneously beating vein by cardiomyocyte transplantation in the wall of the inferior vena cava in a rat: A pilot study, *Journal of Vascular Surgery* 45, 817-820 (2007) (published online), both of which are incorporated by reference herein). Kloner et al. showed that such a cellular graft can generate measurable pressure within the vessel (W. Dai, S. L. Hale, R. A. Kloner, Cardiac cells implanted within the outer aortic wall of rats generate measurable contractile force, *Regenerative Medicine* 1, 119-124 (2005) (published online), incorporated by reference, herein).

However, while such device may be use to affect wave dynamics within the vasculature, it would be very helpful to provide an adjustable device to selectively control wave reflections in order to achieve both improved wave dynamics and increased (or at least non-diminished) blood flow to the various organs within the cardiovascular system.

SUMMARY

Vascular resistance in large arteries is composed of a primary viscous component and a dynamic component. The dynamic component is related to the wave characteristics of pulsatile fluid flow through such arteries. These wave characteristics include frequency (heartbeat), amplitude (stroke volume), wavelength, and pressure-flow phase difference (which depends on the elastic and viscoelastic properties of the carrier vessel). The frequency-dependent component of vascular resistance is known as "impedance." Essentially, this dynamic component (e.g., dynamic resistance) is the response of the vascular system as a compliant system to the pressure and wall expansion waves that originate at the root of the aorta during the systolic phase of the cardiac cycle.

Furthermore, pressure wave reflection from branching points (renal arteries etc.), or from sudden changes in the arterial wall properties (e.g., thickness, diameter or stiffness) can grossly change the resistance that the heart experiences during the cardiac cycle. Stiffening of the aorta due to aging or vascular diseases, for instance, hampers the ability of blood vessels to vasodilate. This effect is a major source of elevated systemic resistance and thus blood pressure. Such stiffening also results in a change in the wave speed and length of forward propagating waves as well as the nature of their interaction with the reflective waves.

While efforts have been made trying to elucidate the role of wave reflections in heart failure and clinical studies have confirmed that abnormal pulsatile loads play an important role in the pathogenesis of left ventricular hypertrophy (LVH) and congestive heart failure (CHF), conventional cardiology in general ignores this wave dynamic and its impact on the vascular resistance mainly due to the complexity of the wave interaction process.

The use of one or more static rings in the vasculature may be used to at least partially control certain wave reflections within the aorta, for example, to reduce the workload of the heart. However, use of such static rings alone may have the undesirable effect of reducing (or increasing) blood flow to certain organs in communication with the cardiovascular system. For example, blood flow to the coronary arteries, the carotid arteries, and/or the renal arteries may be affected in an undesirable way.

Accordingly, the present invention provides methods and devices aimed at creating and/or magnifying artificial reflected waves in the vascular system for the purpose of achieving both reducing a cardiac load while improving, or at least not negatively affecting, blood flow to various organs in communication with the cardiovascular system.

In one embodiment, there is provided a system configured to be at least partially implanted in mammal along an aorta, the system comprising: an inelastic member comprising a biocompatible material, the inelastic member configured to surround at least a portion of an outer surface of an aorta at a first location along the aorta; and a pinching member comprising a second biocompatible material, the pinching member configured to surround at least a second portion the outer surface of the aorta at a second location along the aorta, wherein the pinching member is further configured to receive an activation signal at an activation rate and in response to the activation signal, repeatedly compress the aorta at the second location at the activation rate to pump fluid within the aorta in a desired pumping direction.

The pinching member may comprise one or more of: a synthetic biocompatible material, living cells, a tissue-derived matrix or a hydrogel. The pinching member may comprise cardiomyocytes. The system may further comprise an actuator configured to activate the pinching member to compress the aorta in response to the activation signal. The pinching member may comprise first and second arms, wherein the actuator is configured to cause a distance between the first and second arms to decrease and increase in response to the activation signal. The system may further comprise a control unit configured to generate the activation signal and transmit the activation signal to the pinching member. The control unit may be further configured to be implanted within the mammal. The control unit may be further configured to set the activation rate to a first frequency value to cause a first wave dynamic property during a systolic phase of a cardiac cycle, and set the activation rate to a second frequency value to cause a second wave dynamic property during a diastolic phase of the cardiac cycle, wherein the first wave dynamic property is different than the second wave dynamic property. The first wave dynamic property may correspond to a reduction in cardiac load on a heart and wherein the second wave dynamic property corresponds to an increase in blood flow to coronary arteries of the heart.

The system may further comprise a power supply configured to deliver electrical power to the pinching member, wherein the pinching member is configured to use the electrical power to repeatedly compress the aorta in response to the activation signal. The pinching member may be further configured to generate a wave within the aorta in a first direction when the activation rate is a first frequency value and generate a wave within the aorta in a second direction opposite the first direction when the activation rate is a second frequency value different than the first frequency value. The control unit may be further configured to select the activation rate to increase blood flow to carotid arteries of the mammal. The control unit may be configured to select the activation rate to increase blood flow to renal arteries of the mammal. The control unit may be further configured to control a magnitude of a wave created within the aorta in response to the compression of the aorta by the pinching member.

The inelastic member may be configured to generate a reflected wave in the direction of a heart of the mammal in response to blood flow through the aorta, and the pinching member may be further configured to reduce or eliminate the reflected wave prior to the reflected wave reaching the heart. The system may further comprise a second inelastic member, wherein the second inelastic member is configured to be positioned upstream from the elastic member, and to at least partially reflect in the direction of the elastic member, a reflected wave received from the elastic member in response to blood flow through the aorta.

The pinching member may be further configured to generate a pressure wave within the aorta in response to compressing the aorta, and wherein the inelastic member is configured to generate a reflected wave in response to receiving the pressure wave. The inelastic member may be configured to generate the reflected wave towards one or more of: a heart, carotid arteries, or renal arteries of the mammal.

The system may further comprise a second inelastic member comprising the biocompatible material, the second inelastic member configured to surround at least a portion of the outer surface of the aorta at a third location along the aorta. The system may further comprise a second pinching member comprising the second biocompatible material, the second pinching member configured to surround at least a portion the outer surface of the aorta at a third location along the aorta.

In another embodiment, a method of enhancing blood flow within a blood vessel comprises: providing an inelastic member comprising a biocompatible material around at least a portion of an outer surface of an aorta at a first location along the aorta; providing a pinching member comprising a second biocompatible material around at least a second portion the outer surface of the aorta at a second location along the aorta; selecting an activation rate corresponding to a desired aorta compression rate, wherein the pinching member is configured to receive an activation signal at the activation rate; and repeatedly compress the aorta at the second location at the activation rate to pump fluid within the aorta in a desired pumping direction.

The pinching member may comprise one or more of: a synthetic biocompatible material, living cells, a tissue-derived matrix or a hydrogel. The pinching member may comprise cardiomyocytes. The method may further comprise activating the pinching member to compress the aorta in response to the activation signal with an actuator. The pinching member may comprise first and second arms, and wherein activating the pinching member comprises causing a distance between the first and second arms to decrease and increase in response to the activation signal.

The method may further comprise generating the activation signal and transmitting the activation signal to the pinching member using a control unit. The method may further comprise implanting the control unit within the mammal. The method may further comprise setting the activation rate to a first frequency value to cause a first wave dynamic property during a systolic phase of a cardiac cycle, and setting the activation rate to a second frequency value to cause a second wave dynamic property during a diastolic phase of the cardiac cycle, wherein the first wave dynamic property is different than the second wave dynamic property.

The first wave dynamic property may correspond to a reduction in cardiac load on a heart and the second wave dynamic property may correspond to an increase in blood flow to coronary arteries of the heart. The method may further comprise providing a power supply configured to deliver electrical power to the pinching member, wherein the pinching member is configured to use the electrical power to repeatedly compress the aorta in response to the activation signal.

The method may further comprise generating a wave within the aorta in a first direction when the activation rate is a first frequency value and generating a wave within the aorta in a second direction opposite the first direction when the activation rate is a second frequency value different than the first frequency value. The method may further comprise selecting the activation rate to increase blood flow to carotid arteries of the mammal. The method may further comprise selecting the activation rate to increase blood flow to renal arteries of the mammal. The method may further comprise controlling a magnitude of a wave created within the aorta in response to the compression of the aorta by the pinching member.

The method may further comprise generating a reflected wave in the direction of a heart of the mammal in response to blood flow through the aorta, and reducing or eliminating the reflected wave prior to the reflected wave reaching the heart. The method may further comprise providing a second inelastic member, and positioning the second inelastic member upstream from the elastic member, and at least partially reflecting in the direction of the elastic member, a reflected wave received from the elastic member in response to blood flow through the aorta.

The method may further comprise generating a pressure wave within the aorta in response to compressing the aorta, and generating, with the inelastic member, a reflected wave in response to receiving the pressure wave. The method may further comprise, with the inelastic member, generating the reflected wave towards one or more of: a heart, carotid arteries, or renal arteries of the mammal. The method may further comprise providing a second inelastic member comprising the biocompatible material, and surrounding, with the second inelastic member, at least a portion of the outer surface of the aorta at a third location along the aorta. The method may further comprise providing a second pinching member comprising the second biocompatible material, and surrounding, with the second pinching member, at least a portion the outer surface of the aorta at a third location along the aorta.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification, including definitions, will control. In addition, the materials, methods, and examples are illustrative only and not intended to be limiting. All patents and publications cited in this specification are incorporated herein by reference in their entirety. These and other embodiments are described in greater detail below with reference to FIGS. 1-4.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

Figure 1:
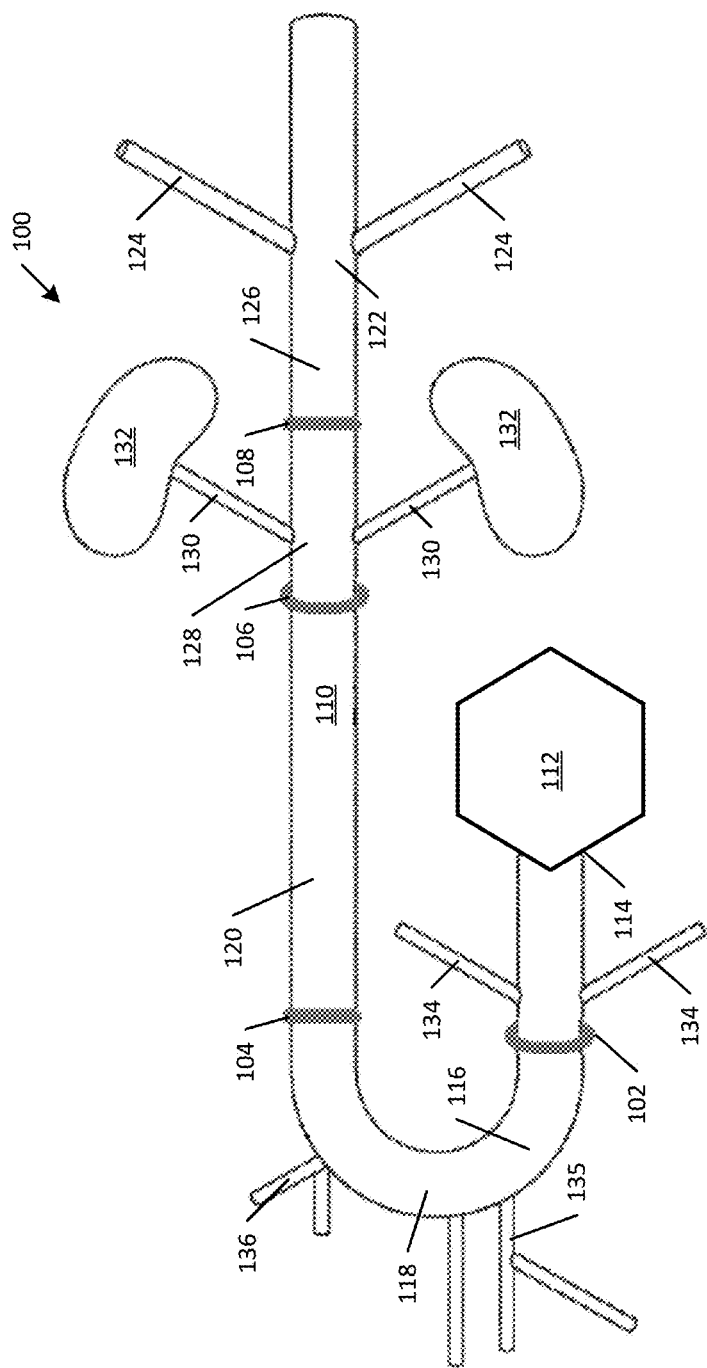
FIG. 1 illustrates one embodiment of a dynamic wave reflection system configured as a left ventricular assist device.

The wave reflection process in large vessels such as the aorta, superior and inferior vena cava, etc. can be optimized, boosted, and controlled to improve the performance of major end-organs, by optimizing blood flow to the heart, brain, kidney, and liver (and other organs). Such results may be achieved by using a combination of static, passive reflection sites (e.g. synthetic or biologic ring or band) on the wall of the vessel in the proximity of a dynamic and active pincher (e.g., a cardiomyocyte graft, a deformable dynamic ring, a deformable clip (such as a C-shaped clip), a tissue-derived hydrogel or matrix, etc. or a combination of such pincher embodiments). Such a device can be personalized based on state of an individual cardiovascular system to favor a specific organ hemodynamically based on clinical need. In one embodiment, the proposed system is configured to create, trap and control reflected as well as propagated waves using various combinations of synthetic and biologic materials. The parameters manipulated to control, create and optimize hemodynamic waves include, but are not limited to one or more of: (1) location of the static, passive reflections site(s) along the vessel; (2) distances between the static, passive reflection sites; (3) distance between the dynamic, active pincher and static passive reflection site; (4) heart rate (e.g., which can be controlled in some embodiments via communication with an implantable cardiac rhythm management device, such as a pacemaker); (5) frequency of the excitation of the dynamic, active pincher; (6) characteristics of the synthetic material used; and/or (7) characteristics of the biologic or cellular materials used.

Cardiac wave reflection can result in added positive (downstream) or subtracted negative (upstream) pumping effect in flow loops that consist of a compliant tube connected to well-defined reflective sites. Using tubes with dimensions similar to the adult human aorta and with similar compliance properties, one can produce forward or retrograde mean flow by simply changing the frequency and/or duty cycle of pulsatile flows. The observed pumping effects are due to the positive and negative interaction between incoming and reflective waves at the reflection sites.

The wave reflection process in parts of the vascular system, e.g., the aorta, etc. can be manipulated by placing one or more static, rigid, fixed inner and outer diameter rings (sometimes referred to as a static reflection-changing elements, or bands) around the aorta to create new wave reflection sites. These wave reflection manipulations can result in constructive interaction with reflective waves to produce a forward pumping effect and/or to correct an adverse pumping effect that may exist due to negative interactions between forward waves and reflective waves. These interactions are complex. In a healthy, young adult, the pressure wave originating from the heart can be traveling at the speed about 6 m/s in the aorta, making several rounds in the aorta and the rest of the arterial system in the duration of a single heartbeat. Therefore, before a cardiac pressure wave dies out, reflections stemming from it could encounter other waves in additive/constructive or interruptive/destructive manners due to phase differences. In the case of a constructive interaction, the reflective wave serves as a net forward flow (positive, downstream, away from the heart). The pump (or the heart) receives added help from a compliant tube (the aorta) due to its ability to provide additional pumping in series with the main pump (heart), reducing the heart's overall loading. In the case of a destructive interaction, the reflective wave serves as a net retrograde flow (negative, upstream, towards the heart). The pump (or the heart) is presented with additional resistance since the elastic tube (or aorta) now acts as an anti-pump against the pump's (or the heart's) output.

The use of such static rings alone provides various advantages by creating wave reflection in the vascular system in order to create constructive interactions between existing wave dynamics and reflective waves for the purpose of increasing net forward flow or reducing vascular impedance. This lowers the workload on the heart and increases cardiac output, providing a viable option for the prevention and treatment of many heart conditions and diseases, especially those associated with different types of heart failure such as congestive heart failure (CHF), acute heart failure (AHF), systolic heart failure, and heart failure with preserved ejection fraction (HFpEF). For example, patients with hypertension (high blood pressure) of any type (essential hypertension, secondary hypertension, isolated systolic hypertension, or resistant hypertension) and left ventricular hypertrophy (LVH) who are in danger of suffering from heart failures can benefit from such static rings as reduction of pulsatile load through the present techniques can significantly improve left ventricular (LV) function in patients. However, such static ring systems have various disadvantages, as well.

For example, while the static ring system may increase blood flow to certain desired vasculature pathways or reduce cardiac load on the heart, it is difficult, if not impossible, to achieve both. In addition, while causing a desired increase in blood flow to certain organs, the static ring systems may simultaneously cause an undesirable decrease in blood flow to others. To correct these potential disadvantages, one or more dynamic pinching members are provided and strategically positioned around and along the aorta.

Each dynamic pinching member is sized to contact the outer surface of the aorta without significantly compressing it or without compressing it at all. When activated, such as by an electrical activation signal (or other control signal), the dynamic pinching member changes from a relaxed state to an activated state in which it changes diameter, or otherwise activates its pinching mechanism to compress the outer surface of the aorta. Such compression results in a compression of the inside luminal wall of the aorta, as well. When the inside luminal wall of the aorta is compressed, a dynamic pulsatile wave is generated within the blood flowing though the aorta. The dynamic waves propagate in opposite directions from the pinching site. However, as the dynamic waves interact with one or more static rings, a net positive or negative wave propagation direction may be realized.

In addition, the dynamic pinching member is configured to receive the activation signal at an activation rate, which results in dynamic wave generation at the activation rate. The frequency of the activation signal may be changed by a controller and/or manually programmed by a user. For example, in one embodiment, as described below, the controller may select a first activation rate during the systolic phase of the cardiac cycle and a different, second activation rate during the diastolic phase of the cardiac cycle. Changing the activation rate can have the beneficial effect of causing a net positive wave direction during the systolic phase (when the aortic valve of the heart is open), thereby reducing the cardiac load on the heart, and net negative wave direction during the diastolic phase (when the aortic valve of the heart is closed), thereby increasing blood flow to the coronary arteries of the heart.

The amplitude of the activation signal may be modulated as well. An increased amplitude results in a larger compression of the dynamic pinching member during its activation state, which causes a larger amplitude dynamic wave to form within the aorta.

Using the techniques described below, a user can easily maximize or optimize hemodynamic performance (e.g., by reducing cardiac workload and/or increasing blood flow to one or more organs (or at least avoid decreasing blood flow to such organs)) by strategically positioning one or more dynamic pinching members and one or more static rings around the aorta, and by modifying one or more of the frequency or amplitude of the activation signal used to activate the one or more dynamic pinching members.

One form of the static reflection-changing element is a band, which can include a strip of material configured to have curvature for constricting part of the vasculature and can fully encircle or partially encircle around a blood vessel. The band can be made of any suitable material, and for implanting purposes, a biocompatible material, such as a metal, an alloy, a plastic, a fabric or a combination of any of the above. In some embodiments, the band is made of one or more malleable materials such that an operator (e.g., a surgeon) can manually adjust its curvature to achieve the right amount of constriction over a selected vascular site. The band can have a variety of configurations that vary in thickness, axial width and diameter. In some embodiments, the band has an axial width between about 4 cm and about 8 cm. In one embodiment, the band is a full-circle ring. The reflection-changing element of the invention is placed or implanted at a predetermined position to create a new reflection site or shift an existing reflection site from its natural position to a new position that is more favorable in terms of added wave pumping capability. The band can be a strip of biocompatible fabric wrapped around that location in a constricting manner similar to a bandage. It can be immobilized using an adhesive or other conventional attachment devices such as a suture. If the band is a full circle ring, it can be an open ring that is closable after being delivered to the desired implanting location. In one embodiment, the ring is secured to the vessel wall by a strip of self-adhesive bandage wrapped around the ring.

FIG. 1 illustrates one embodiment of a dynamic wave reflection system 100. The dynamic wave reflection system 100 of FIG. 1 is particularly well suited to function as a left ventricular assist device by reducing cardiac load on the heart 112. The system 100 includes a first dynamic pinching member 102, a first static reflection-changing element 104, a second dynamic pinching member 106, and a second static reflection-changing element 108. Each member and element 102, 104, 106, 108 is implanted such that it completely or partially surrounds the aorta 110, the largest artery in the human and other mammals. The aorta 110 originates from the left ventricle of the heart 112 at the point of aortic input or aortic root 114, and can be divided into a section called the ascending aorta 116, a section called the Arch of aorta 118, and a section called the descending aorta 120, which ends at the iliac bifurcation 122 where the aorta divides into the common iliac arteries 124. In the lower part of the descending aorta 120 called the abdominal aorta 126, there is also a renal bifurcation 128 where the aorta branches and extends, through renal arteries 130, into the kidneys 132.

As shown in FIG. 1, the first dynamic pinching member 102 is positioned in the ascending aorta 116, downstream from the coronary arteries 134. The first static reflection-changing element 104 is positioned in the descending aorta 120, just downstream from the left subclavian artery 136. The activation frequency of the first dynamic pinching member 102 may be selected to cause waves and wave reflections from the first static reflection-changing element 104 that create a wave traveling in the positive direction (away from the heart).

The activation frequency may be maintained during the entire cardiac cycle. However, in some embodiments, when desired, the activation frequency is controlled such that a wave traveling in the positive direction (away from the heart 112) reaches the heart 112 during the systolic phase of the cardiac cycle (in response to a first activation frequency), and a wave traveling in the negative direction (towards the heart 112) reaches the heart 112 during the diastolic phase of the cardiac cycle (in response to a second, different activation frequency). In this manner, the positive direction wave can reduce cardiac load on the heart and the negative direction wave can increase blood flow to and through the coronary arteries 134.

The dynamic wave reflection system 100 of FIG. 1 also includes an optional second dynamic pinching member 106 and a second static reflection-changing element 108. The second dynamic pinching member 106 is positioned around the descending aorta 120 upstream from and near to the renal bifurcation 128. The second static reflection-changing element 108 is positioned around the descending aorta 120 between the renal bifurcation 128 and the iliac bifurcation 122. Together, the second dynamic pinching member 106 and second static reflection-changing element 108 can be used to increase blood flow to the kidneys 132. For example, an activation frequency may be selected such that the second dynamic pinching member 106 generates a positive, downstream pulsatile wave, directing blood flow towards the renal bifurcation 128, renal arteries 130, and kidneys. The second static reflection-changing element 108 is configured to reflect at least a portion of the generated pulsatile wave in the negative direction, back towards the renal bifurcation 128, renal arteries 130, and kidneys 132. The first static reflection-changing element 104 may also be configured to reflect at least a portion of the generated pulsatile wave in the positive direct, towards the renal bifurcation 128, renal arteries 130, and kidneys 132, as well.

In some embodiments, the dynamic pinching members and static reflection-changing elements 102, 104, 106, 108 (as well as all other dynamic pinching members and static reflection-changing elements described herein) can be implanted at multiple locations in the vasculature at the same time or in sequence. While the members and elements illustrated are placed outside a blood vessel, one skilled in the cardiovascular art should readily understand that any one or all of them can be placed inside a blood vessel, for example, by use of delivery and deployment devices similar to those used with stents and other cardiovascular implants (e.g., a balloon catheter). For example, a collapsible ring, band, graft or stent can be placed over a balloon in a catheter and delivered via the femoral veins to a desired site before being expanded and immobilized against the artery wall as the balloon is inflated.

In one embodiment, the members and elements are delivered percutaneously via any one of the following methods: (1) accessing the aorta through the femoral artery (or radial artery or brachial artery); (2) accessing the vena cava via the internal or external jugular, subclavian, or brachial veins; accessing portal vein via femoral vein or internal jugular vein; (3) delivering the static elements (e.g., ring(s) or bands) to specific location(s) using a commercially available or customized catheter; (4) delivering the dynamic members (e.g., cell-type or artificial or a combination) to a specific vascular site using the same catheter or different set of catheter.

The static reflection-changing elements may be passive in the sense that they are meant to be permanent or semi-permanent implants that, once implanted, would remain the same configuration in the same location for an extended period, possibly for life. Some of the materials suitable for making the static reflection-changing elements include fabrics such as silk, polyester (e.g., sold under the trade name Dacron®), shape memory alloys and thermoplastic polymers such as polyethylene (PE) and polytetrafluoroethylene (PTFE). Moreover, there in some embodiments, a dynamic pinching member may function as a static reflection-changing element by maintaining the dynamic pinching member is an activated state instead of periodically activating and deactivating the dynamic pinching member at an activation frequency.

The dynamic pinching members may be made according to any of the embodiments described herein. In some embodiments the dynamic pinching members can be made of synthetic biocompatible materials, living cells (autologous or allogeneic), tissue-derived matrices or hydrogels or combinations of these materials. In some embodiments, the pinching member is provided as an electrical stimulator and pinching is accomplished by stimulating the local muscle around the vessel such as aorta and vena cava with the pinching member/electrical stimulator.

Figure 2:
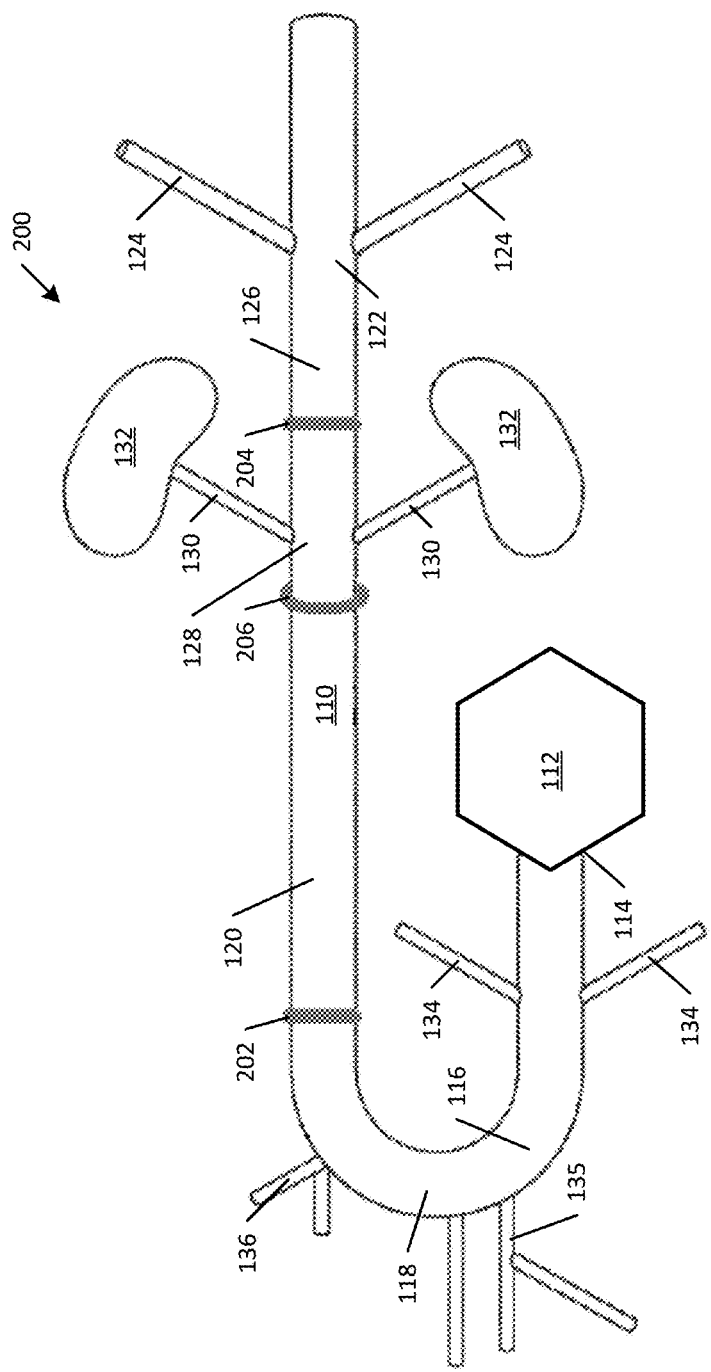
FIG. 2 illustrates one embodiment of a dynamic wave reflection system configured as a renal assist device.

FIG. 2 illustrate another embodiment of a dynamic wave reflection system 200. The dynamic wave reflection system 200 of FIG. 2 is particularly well suited to function as a renal assist device. This system 200 is configured to increase renal blood flow (e.g., for patients suffering from renal and/or heart failure, as well as patients with liver disease and various forms of shock) to improve renal function. The system 200 includes two static reflection-changing elements 202, 204 and one dynamic pinching member 206. As discussed above, in some embodiments, the pincher merely includes an electrical stimulator that is configured to stimulate the targeted vessel to contract and generate the waves. The first static reflection-changing element 202 is positioned in the descending aorta 120, just downstream from the left subclavian artery 136.

The dynamic pinching member 206 is positioned around the descending aorta 120 upstream from and near to the renal bifurcation 128. The second static reflection-changing element 204 is positioned around the descending aorta 120 between the renal bifurcation 128 and the iliac bifurcation 122. Together, the dynamic pinching member 206 and static reflection-changing elements 202, 204 can be used to increase blood flow to the kidneys 132. For example, an activation frequency may be selected such that the dynamic pinching member 206 generates a positive, downstream pulsatile wave, directing blood flow towards the renal bifurcation 128, renal arteries 130, and kidneys. The second static reflection-changing element 204 is configured and positioned to reflect at least a portion of the generated pulsatile wave in the negative direction, back towards the renal bifurcation 128, renal arteries 130, and kidneys. The first static reflection-changing element 202 is configured and positioned to reflect at least a portion of the negative, upstream generated pulsatile wave in the positive direction, back towards the renal bifurcation 128, renal arteries 130, and kidneys, as well.

Figure 3:
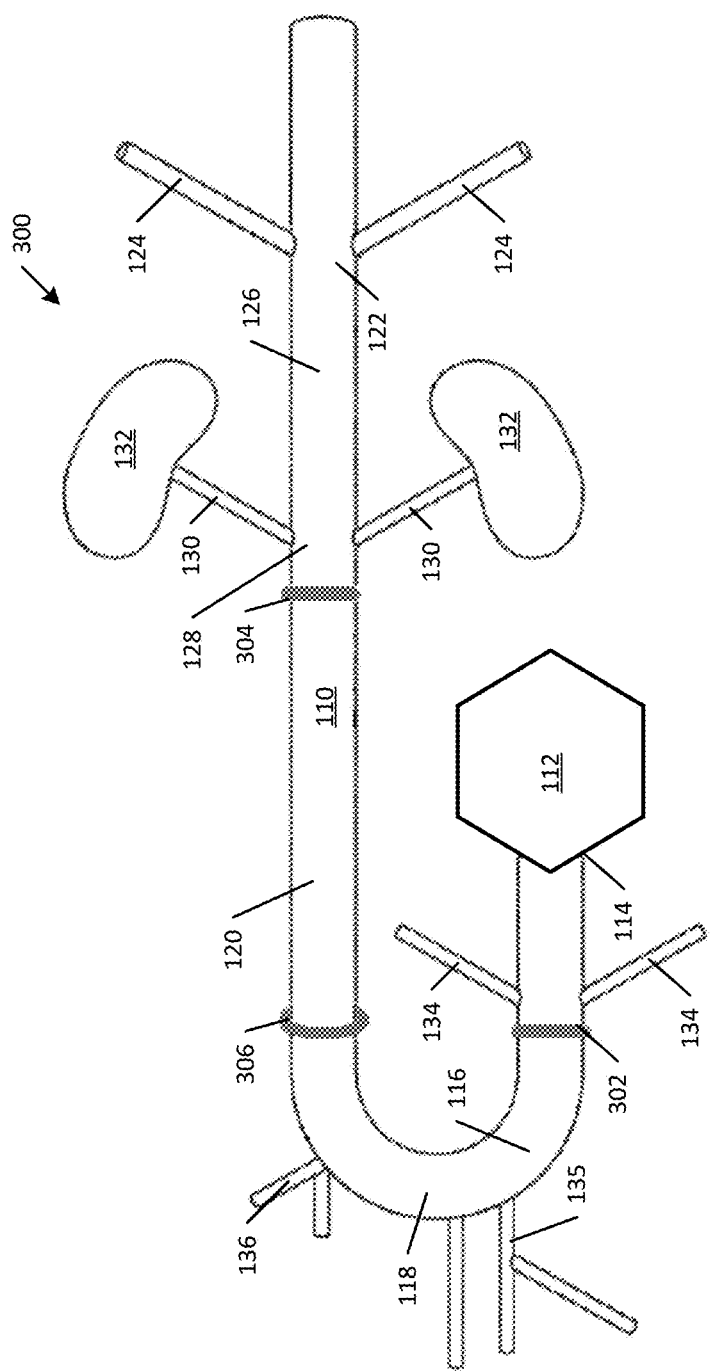
FIG. 3 illustrates one embodiment of a dynamic wave reflection system configured as a cerebrovascular disease assist device.

FIG. 3 illustrates another embodiment of a dynamic wave reflection system 300. The dynamic wave reflection system 300 of FIG. 3 is particularly well suited to function as a cerebrovascular disease assist device (CDAD) by dynamically controlling and increasing cerebral blood flow. The system 300 includes first and second static reflection-changing elements 302, 304 and a dynamic pinching member 306. Each member and element 302, 304, 306 is implanted such that it completely or partially surrounds the aorta 110.

As shown in FIG. 3, the first static reflection-changing element 302 is positioned in the ascending aorta 116, downstream from the coronary arteries 134. The second static reflection-changing element 304 is positioned around the descending aorta 120 upstream from and near to the renal bifurcation 128. The dynamic pinching member 306 is positioned in the descending aorta 120, just downstream from the left subclavian artery 136. The activation frequency of the dynamic pinching member 306 may be selected to cause waves and wave reflections directed towards the right and left subclavian arteries 135, 136. For example, some waves from the dynamic pinching member 306 are generated in the negative direction, towards the heart 112 and subclavian arteries 135, 136. Some of such waves will reflect off of the first static reflection-changing element 302 and travel in the positive direction, away from the heart 112 and towards the subclavian arteries 135, 136. Other waves from the dynamic pinching member (and reflected waves from the first static reflection-changing element 302) travel in the positive direction, away from the subclavian arteries 135, 136 and reflect off of the second static reflection-changing elements towards 304 back towards the subclavian arteries 135, 136. Such waves and wave reflections control or improve blood flow to the subclavian arteries and through the cerebrovascular system.

The activation frequency may be maintained during the entire cardiac cycle. However, in some embodiments, when desired, the activation frequency is controlled such that waves traveling in the negative direction (towards the subclavian arteries 135, 136 and the heart 112) reach the heart 112 during the diastolic phase of the cardiac cycle so as not to increase the cardiac load on the heart.

Other applications of controlling hemodynamics through wave generation and reflection are possible, as well. For example, systems including one or more dynamic pinching members and static reflection-changing elements may be configured to: (1) control venous return from the brain by implementing a similar system in the internal jugular vein; (2) reduce central venous pressure by implementing similar system on the Vena cava; (3) reduce pressure inside and on an aneurysm by implementing a similar system proximal and/or distal to the aneurysm; (4) assist circulation patterns in patients with congenital heart diseases by implementing a similar system customized to the circulatory defect; (5) control distribution of blood flow to the lungs in patients with congenital heart disease; and/or (6) reduce pulsatile workload on the right ventricle by implementing similar system in the pulmonary arterial circulation system.

Figure 4:
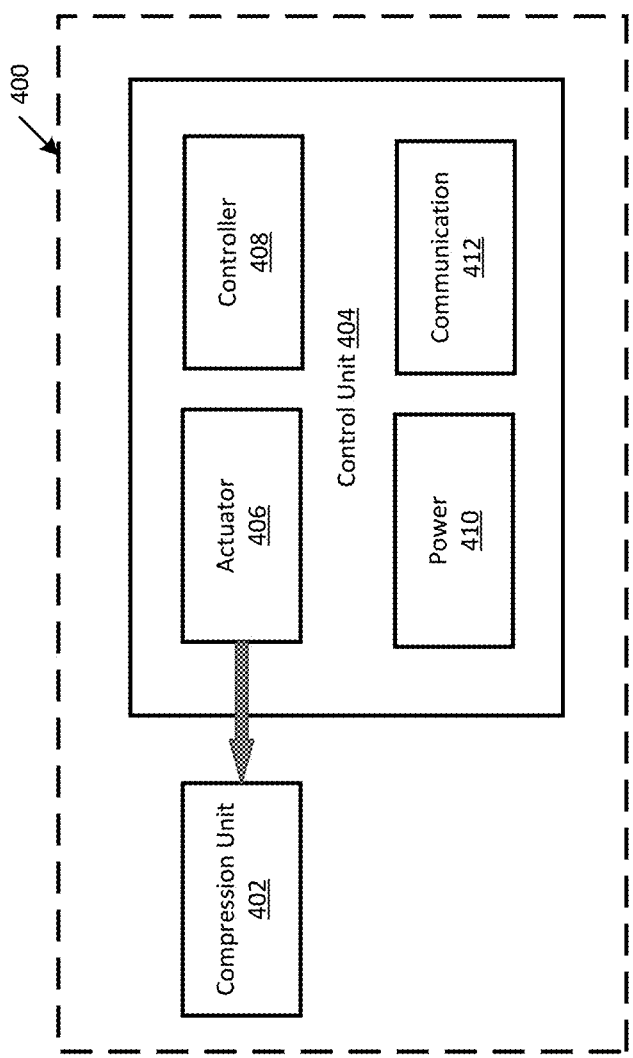
FIG. 4 illustrates one embodiment a dynamic pinching member suitable for use in any of the dynamic wave reflection systems of FIGS. 1-3.

FIG. 4 illustrates one embodiment of a dynamic pinching member 400, which can be any dynamic pinching member 102, 106, 206, 306 described herein. The dynamic pinching member 400 includes a compression unit 402 and a control unit 404. The compression unit 402 is configured to apply a pinching or compression force to the outside surface of a blood vessel when activated. In some embodiments, such as when the dynamic pinching member 400 is configured to be deployed within the vasculature (e.g., within a lumen of the aorta, etc.), the compression unit 402 may be configured to activate a pumping member, such as by contracting a membrane, squeezing a tube, or activating a piston, etc. The control unit 404 is configured to control the activation of the compression unit 402.

In one embodiment, the control unit 404 includes an actuator 406, a controller 408, a power supply 410 and a communication unit 412. The actuator 406 is configured to deliver electrical and/or mechanical energy to the compression unit 402 and to cause the compression unit 402 to change between activated and inactivated states (e.g., compressing and non-compression). In one embodiment, the actuator includes a motor, magnet, fluid tubing line, and/or electrical conductor.

The controller 408 is configured to generate an activation signal to cause the actuator to activate and deactivate the compression unit. For example, the controller 408 may be configured to generate a square pulse wave at a programmed activation frequency. In some embodiments, the controller 408 also includes a memory (not shown) that stores instructions that when executed cause the controller to perform desired operations. One such operation can include enabling remote communication and programming of the dynamic pinching member 400.

The power supply 410 is configured to store electrical energy, and to provide such energy to the components 402, 404, 406, 408, 4012 of the dynamic pinching member 400, as needed. In some embodiments, the power supply 410 includes a battery and/or a capacitor. The communication unit 412 is configured to enable communication between the dynamic pinching member 400 and other implanted and/or external (non-implanted) devices. For example, the communication unit 412 may include a transmitter and/or a receiver to enable wired and/or wireless communications, e.g., via Bluetooth, IEEE 802.11 a/b/g/n, near field communication (NFC), RF communication, etc. In one embodiment the communication unit 412 is configured to communicate with an implanted cardiac rhythm management device. The communication unit 412 can send and/or receive information and/or programming to or from the cardiac rhythm management device. In another embodiment, the communication unit 412 is configured to communicate with an external programing device, and to receive programming instructions (e.g., activation rate, activation amplitude (e.g., strength of compression unit compression), timing information (e.g., when to utilize a particular activation rate and/or amplitude, such as when one configuration is desired during a systolic phase of the cardiac cycle and a second configuration is desired during a diastolic phase of the cardiac cycle).

In some embodiments, the dynamic pinching member 400 and/or control unit 404 includes less than all of the illustrated components. In some embodiments, two or more of the illustrated components may be combined together. For example, the controller 408 may include the communication unit 412 and/or actuator 406. Similarly, in some embodiments, the compression unit 402 may include the actuator 406. Other combination or element omissions are possible, as well.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material. In the event of a conflict, the conflict is to be resolved in favor of the present disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

Other Considerations

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a", "an", or "the" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others. All such modifications and variations are intended to be included herein within the scope of this disclosure. Further, additional embodiments created by combining any two or more features or techniques of one or more embodiments described herein are also intended to be included herein within the scope of this disclosure.

What is claimed is:

1. A system configured to be at least partially implanted in mammal along an aorta, the system comprising:
    an inelastic member comprising a biocompatible material, the inelastic member configured to surround at least a portion of an outer surface of an aorta at a first location along the aorta; and
    a pinching member comprising a second biocompatible material, the pinching member configured to surround at least a second portion the outer surface of the aorta at a second location along the aorta, wherein the pinching member further comprises an actuator configured to actuate compression of the aorta and a control unit configured to generate an activation signal at an activation rate and transmit the activation signal at the activation rate to the actuator,
    wherein the actuator is configured to receive the activation signal at the activation rate and in response to the activation signal, repeatedly compress the aorta at the second location at the activation rate to pump fluid within the aorta in a desired pumping direction, and
    wherein the actuator is further configured to receive the activation signal at the activation rate during both a systolic period and a diastolic period of a cardiac cycle of a heart of the mammal and in response to the activation signal, repeatedly compress the aorta at the second location at the activation rate during both the systolic period and the diastolic period of the cardiac cycle of a heart of the mammal.

2. The system of claim 1, wherein the pinching member comprises one or more of: a synthetic biocompatible material, living cells, a tissue-derived matrix or a hydrogel.

3. The system of claim 2, wherein the pinching member comprises cardiomyocytes.

4. The system of claim 1, wherein the pinching member comprises first and second arms, and wherein the actuator is configured to cause a distance between the first and second arms to decrease and increase in response to the activation signal.

5. The system of claim 1, wherein the control unit is further configured to set the activation rate to a first frequency value to cause a first wave dynamic property during a systolic phase of a cardiac cycle, and set the activation rate to a second frequency value to cause a second wave dynamic property during a diastolic phase of the cardiac cycle, wherein the first wave dynamic property is different than the second wave dynamic property.

6. The system of claim 5, wherein the first wave dynamic property corresponds to a reduction in cardiac load on a heart and wherein the second wave dynamic property corresponds to an increase in blood flow to coronary arteries of the heart.

7. The system of claim 1, further comprising a power supply configured to deliver electrical power to the pinching member, wherein the pinching member is configured to use the electrical power to repeatedly compress the aorta in response to the activation signal.

8. The system of claim 1, wherein the pinching member is further configured to generate a wave within the aorta in a first direction when the activation rate is a first frequency value and wherein the pinching member is configured to generate a wave within the aorta in a second direction opposite the first direction when the activation rate is a second frequency value different than the first frequency value.

9. The system of claim 1, wherein the control unit is further configured to select the activation rate to increase blood flow to carotid arteries of the mammal.

10. The system of claim 1, wherein the control unit is configured to select the activation rate to increase blood flow to renal arteries of the mammal.

11. The system of claim 1, wherein the control unit is further configured to control a magnitude of a wave created within the aorta in response to the compression of the aorta by the pinching member.

12. The system of claim 1, wherein the inelastic member is configured to generate a reflected wave in the direction of a heart of the mammal in response to blood flow through the aorta, and wherein the pinching member is further configured to reduce or eliminate the reflected wave prior to the reflected wave reaching the heart.

13. The system of claim 1, further comprising a second inelastic member, wherein the second inelastic member is configured to be positioned upstream from the pinching member, and to at least partially reflect in the direction of the pinching member, a reflected wave received from the pinching member in response to blood flow through the aorta.

14. The system of claim 1, wherein the pinching member is further configured to generate a pressure wave within the aorta in response to compressing the aorta, and wherein the inelastic member is configured to generate a reflected wave in response to receiving the pressure wave.

15. The system of claim 14, wherein the inelastic member is configured to generate the reflected wave towards one or more of: a heart, carotid arteries, or renal arteries of the mammal.

16. The system of claim 1, further comprising a second inelastic member comprising the biocompatible material, the second inelastic member configured to surround at least a portion of the outer surface of the aorta at a third location along the aorta.

17. The system of claim 1, further comprising a second pinching member comprising the second biocompatible material, the second pinching member configured to surround at least a portion the outer surface of the aorta at a third location along the aorta.

18. The system of claim 1, wherein the activation rate comprises a first activation rate during the systolic period and a second activation rate during the diastolic period, and wherein the first activation rate is different than the second activation rate.

19. The system of claim 18, wherein the first activation rate reduces cardiac load on the heart by causing a first wave to travel in a positive direction away from the heart during the systolic period and wherein the second activation rate increases blood flow to and through coronary arteries of the heart by causing a second wave to travel in a negative direction towards the heart during the diastolic period.

* * * * *